United States Patent [19]
Riley

[11] Patent Number: 5,586,558
[45] Date of Patent: Dec. 24, 1996

[54] OPTIMIZER MEASURING UNIT

[75] Inventor: David R. Riley, Russellville, Ark.

[73] Assignees: Stanley E. Gately; Catherine G. Gately, both of Russellville, Ark.

[21] Appl. No.: 300,485

[22] Filed: Sep. 2, 1994

[51] Int. Cl.⁶ ........................................... A61B 5/10
[52] U.S. Cl. ............................... 128/781; 128/782
[58] Field of Search ........................ 128/774, 781, 128/782; 33/511, 512

[56] References Cited

U.S. PATENT DOCUMENTS

| | | | |
|---|---|---|---|
| 3,722,103 | 3/1973 | Gregoire | 33/512 |
| 4,033,329 | 7/1977 | Gregory et al. | 128/781 |
| 4,135,498 | 1/1979 | McGee | 128/774 |
| 4,492,236 | 1/1985 | Pile | 128/781 |
| 4,603,486 | 8/1986 | Moroney | 128/781 |

FOREIGN PATENT DOCUMENTS

| | | | |
|---|---|---|---|
| 1326244 | 7/1987 | U.S.S.R. | 128/781 |

*Primary Examiner*—Max Hindenburg

[57] ABSTRACT

The machine of the present invention measures degree angle and anthropometric linear measurements of the skeletal structure of the human body. The individual stands behind the machine with the top of their sternoclavicular joint at 0 degree line. Because every individual is measured from the same beginning point a study can be done according to the data collected. From here 10 componet variables are taken with the measuring unit. These variables are entered into a computer data base for calculation. This now begins an infield study of individual workers at a work station or exercise on a resistance training program and or undergo medical treatment for biomechanical correction. Studying repetitive motion injuries in the work force is one example. (non-surgical). By measuring bone lengths and degree angles of a human body we have found that certain characteristics or trends can be found by this systematic measuring procedure. For example we have found that clients with equal bone lengths in upper legs (femur) and torso length, plus a shorter length in lower leg (tibia) have a 0 degree torso deflection range, these individuals experience chronic low back pain. This means these individuals are at extremely high risk of experiencing a lower lumbar injury that can injure them greatly. 9 other graphs are generated so reaching, bending, twisting, pressing, pulling, and sitting can be broken down into exact biomechanical movements for a specific muscle range group. All measurements are taken with the individual standing behind the measuring unit in a relaxed posture.

9 Claims, 3 Drawing Sheets

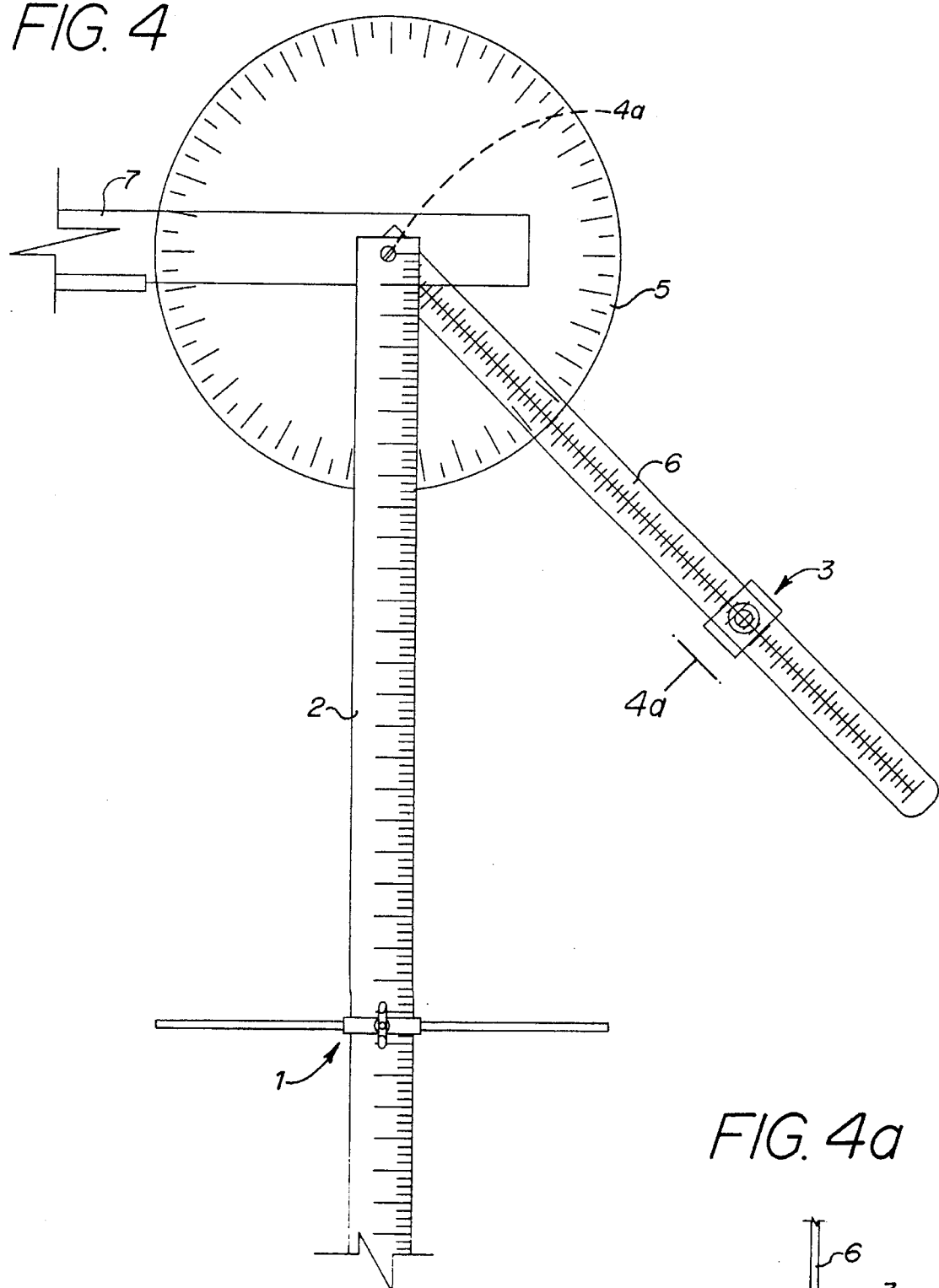
FIG. 4
FIG. 4a
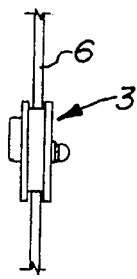

5,586,558

OPTIMIZER MEASURING UNIT

BACKGROUND OF THE INVENTION

This invention was developed to determine natural ranges of motion of any spacific individual. These anthropometric measurments are used in providing job safety for the work force and safety for individuals using a kinetic exsersise program. By obtaining the 10 componet varibles by using the Optimizer Measuring unit the ergonomic or health care professional can now fit the individual with the proper safety appartus appropriate for that individual in the job task they are performing. Not only can we determine the correct safety appartus but we can also collect data on certian characteristics of the human body and find trend and tendency patterns of certian ranges of motion that are at a higher risk of developing a repetitive motion injury while performing a spacific job task. This also addresses the problem of adjusting a work station to relieve any wasted motion that is out of that persons natural range of motion. By taking into account that each person is measured in the same systematic way true data can be analised and compared over time to zero in on spacific problem areas, and correct those areas even quicker to reduce repetitive motion injuries in the work force. By this measuring unit height is no longer a factor, because this device has a begining or point of origin from which all measuring data is collected, (which is the top of the sternoclavicular joint or sternal notch of the human body) and can adjust to the height of the individual being measured it makes it simple to use and process data. As the rest of this applaction is reviewed it will become more clear as to the application of said measuring unit.

SUMMARY OF THE INVENTION

The invention is composed of a metal stand and a metal base plate. The stand when retracted is 4 feet in height and extends to 6 feet 8 inches in height. It has metal arms that extend from the stand to right and from the stand to left. Arms are 16 inches in length. These arms are made of metal and have a measuring apparatus attached to the end of each arm. The measuring apparatus attached to the metal arm to right is a plexiglass disc 10 inches in diamenter. This disc also has one degree graduations etched on its surface from 0 to 360. Attached to this disc at the center point is a torso rule 30 inches in length and 2 inches wide, there are graduations etched onto this rule in ¼ inch increments. Measurements start at 0 inches and read through 30 inches. Mounted on the torso rule is a metal slide assembly, it is 12 inches in length, 5 inches to the right and 5 inches to the left 2 inches on the torso rule itself. This torso rule slide is ¼ inch square tubing and adjust up and down vertically on the rule to measure torso lengths. Also attached to the disc at the center point is the radial dial arm this is made of plexiglass ⅛ inch thick and 24 inches long. This radial dial arm has ¼ inch graduations etched on the surface. They start at 0 inches and run through 24 inches. Mounted on the radial dial arm is a metal slide with a penlight assembly, this assembly slides up and down the radial dial arm. This slide is used for accurate Measurements. From stand to left is a metal arm and at the end of it is a half circle flat disc mounted to the arm. This disc is ⅛ inch thick and 22 inches in diamenter, graduations in one degree increments from 0 to 90 degrees and 90 to 0 degree are etched on the surface along the outer edge. In the center of the disc where 0 degree to 0 degree is in a straight line an directly from 90 degrees in a straight line to the furthest edge is 0 line or point of origin. Attached to this point is a dial arm made of metal and is 10.5 inches long ⅛ inch thick and 1 inch wide it also comes to a point where the graduations start on the flat disc, this dial is used for pointing to the exact degree measurement.

BRIEF DESCRIPTION OF THE DRAWINGS

FIG. 4 is a plan view of the measuring apparatus on the right of the stand unit in detail on extention arm illustrated in FIG. 1; FIG. 4A is a detail view of the slide on the radial dial arm.

DETAILED DESCRIPTION OF THE PREFERRED EMBODIMENT SECTION (A) EMBODIMENT

Figure 1:
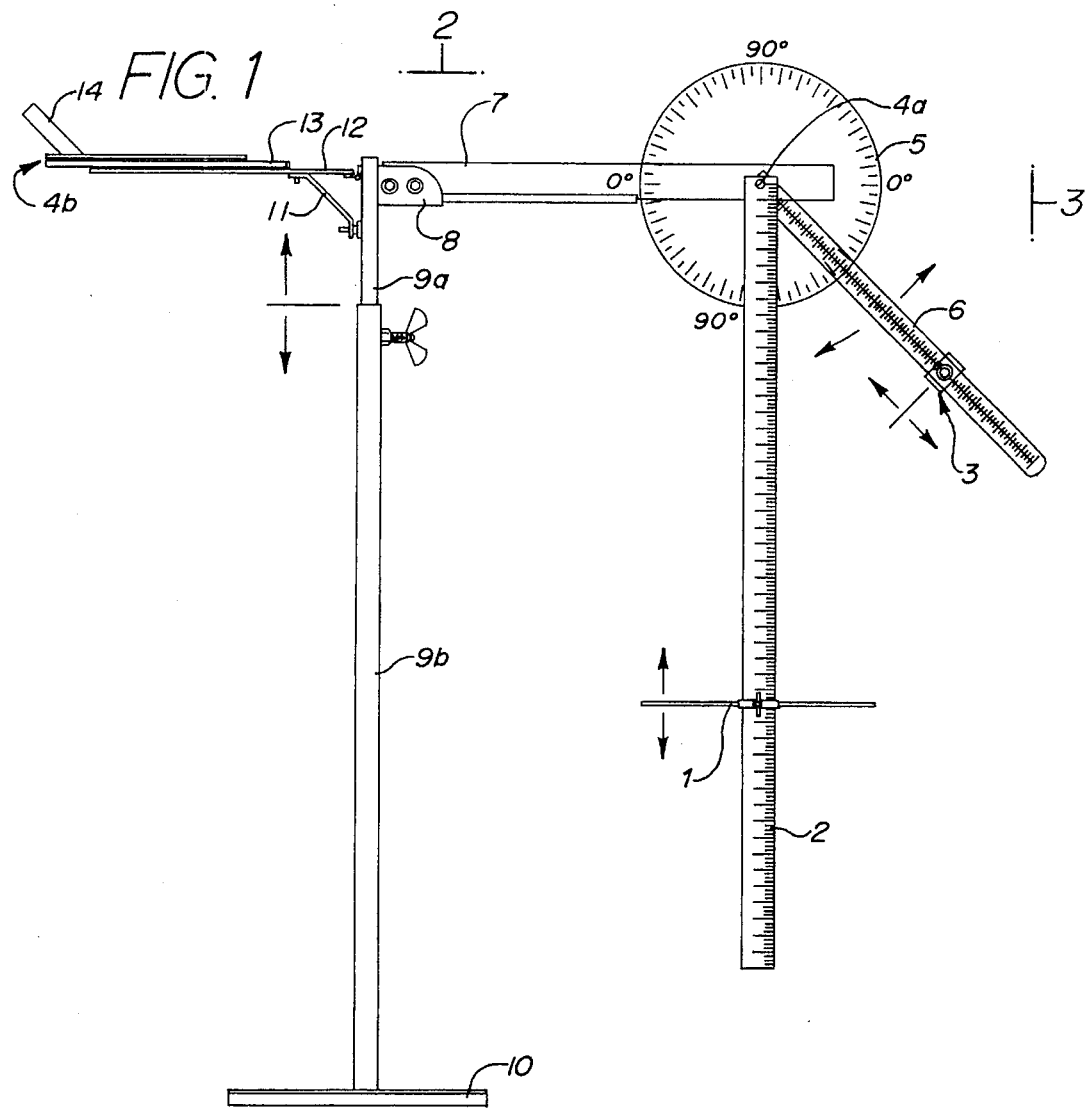
FIG. 1 is a front view of the optimizer measuring unit embodying features of the present invention.
Figure 2:
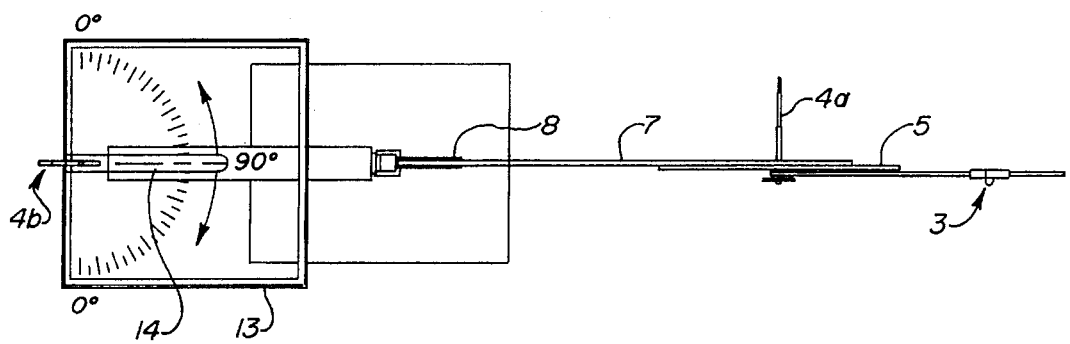
FIG. 2 is a plan view of the machine illustrated in FIG. 1.
Figure 3:
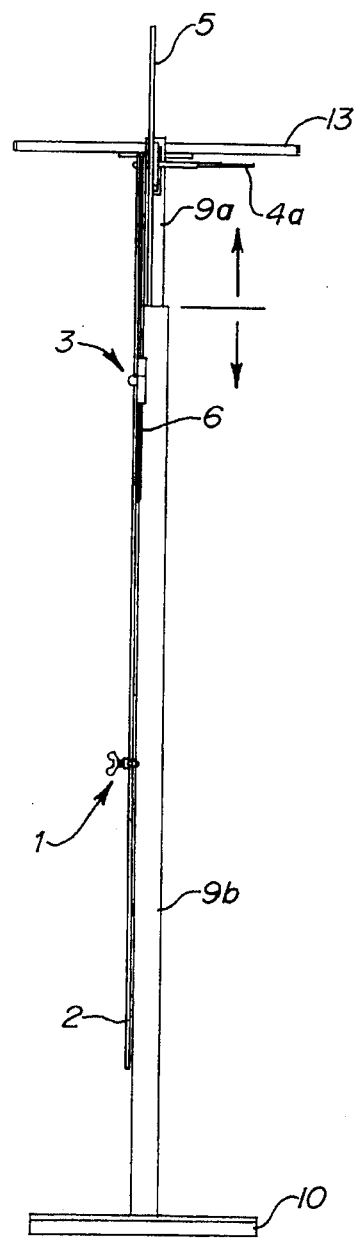
FIG. 3 is a side elevation view of the machine illustrated in FIG. 1.
Figure 5:
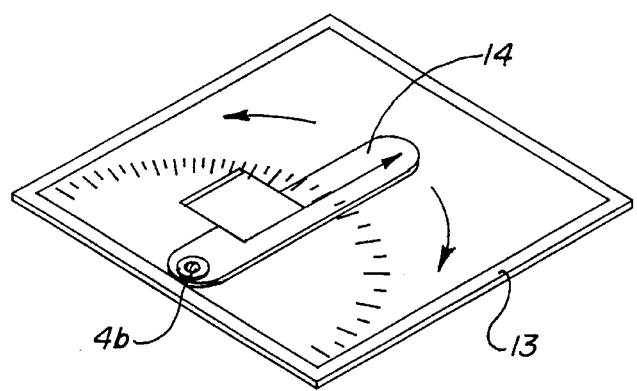
FIG. 5 is a plan view of the flat half protractor on the end of the left arm extention with arm dial assembly illistrated on FIG. 2.

The invention is composed of a metal stand 9a, 9b and a metal base plate 10. The stand 9a, 9b when retracted is 4 feet in height and extends to 6 feet 8 inches in height. It has metal arms 7, 12 that extend from the stand 9a, 9b to right and from stand 9a, 9b to left. Arms 7, 12 are 16 inches in length. These arms 7, 12 are made of metal and have a measuring apparatus attached to the end of each arm 7, 12. The measuring apparatus attached to the metal right support arm is a plexiglass disc 5 which is 10 inches in diameter. This disc 5 also has one degree graduations etched on its surface from 0 to 360. Attached to this disc 5 at the center point 4a is a torso rule 230 inches in length and 2 inches wide, there are graduations etched onto this rule 2 in ¼ inch increments. Measurements start at 0 inches and read through 30 inches. Mounted on the torso rule 2 is a metal slide assembly 1, it is 12 inches in length, 5 inches to the left and 5 inches to the right and 2 inches on the rule 2 itself. This torso rule slide 1 is a 2 inch square metal bracket and adjust up, and down vertically on the torso rule 2 to measure the length of the human torso in inches. Also attached to the plexiglass disc 5 at the center point 4a is the radial dial arm 6, this is made of plexiglass ⅛ inch thick and 24 inches long. This radial dial arm 6 has ¼ inch graduations etched on the surface. They start at 0 inches and run through 24 inches. Mounted on the radial dial arm 6 is a metal slide 3 with a penlight assembly, this slide 3 slides up and down the radial dial arm 6. This slide 3 is used for accurate Measurements of lengths and degrees of the upper extremities of the human body. From stand to left is a metal left support arm 12, and at the end of the metal left support arm 12 is a half circle flat disc 13 mounted to the left support arm 12. This half circle flat disc 13 is ⅛ inch thick and is a 22 inch radius, graduations in one degree increments from 0 to 90 degrees and 90 to 0 degrees are etched on the surface along the outer edge. In the center of the half circle flat disc 13 in a straight line to the furthest edge is 0 line. At the center of the 0 line is pivot point 4b. Attached to this pivot point 4b is the depth angle protractor dial arm 14 used for finding the degree angle of the clavicle on a horizontal plane.

DETAILED DESCRIPTION OF THE PREFERRED EMBODIMENT SECTION (B) EMBODIMENT DRAWINGS REFERENCE

The machine has a base plate 10 from which a vertical extending column 9b is supported. Column 9b is attached to base plate 10 by gusset welds. Inside column 9b is a vertical extending column tube 9a which extends out of column 9b for height adjustment of the measuring unit up and down on a vertical plane. At the top of tube 9a to the right of tube 9a is bracket 8 which is secured to tube 9a. Bracket 8 extends out 2 inches and right support arm 7 is secured to bracket 8 at tube 9a. Right support arm 7 extends out on a horizontal plane where disc 5 is mounted to right support arm 7 at center point 4a. 0 degree line is established at center point 4a and follows a straight line on a horizontal plane. 90 degree line follows a straight line on a vertical plane through center point 4a. Both are etched on disc 5 as black graduations in one degree increments. At center point 4a on right support arm 7 and disc 5 is radial dial arm 6 which is secured to center point 4a. Radial dial arm 6 rotates around center point 4a counter clockwise and clockwise, center point 4a is the pivot point for radial dial arm 6. Secured to radial dial arm 6 is slide 3. Slide 3 slides up and down radial dial arm 6 to pinpoint measurements on the human bodies upper extremities. Slide 3 slides on radial dial arm 6 over the etched graduations on radial dial arm 6. These graduations on radial dial arm 6 start at center point 4a on zero inches and run through the twenty four inch mark. Also at center point 4a is torso rule 2 it extends downward from center point 4a in a vertical plane. Zero inches begin at center point 4a downward and ends at the thirty inch mark. Torso rule 2 is divided into ¼ inch increments with the graduations etched onto the surface of torso rule 2. Secured to torso rule 2 is rule slide 1, this rule slide assembly moves up and down torso rule 2 manually. Rule slide 1 slides vertically on torso rule 2 for the purpose of obtaining accurate measurements of the human torso.

From tube 9a to the left is left support arm 12 which is supported by support 11. Support 11 is secured to tube 9a and secured to left support arm 12 for support of left support arm 12. Left support arm 12 extends out as a support arm for half circle flat disc 13. Half circle flat disc 13 is a plexiglass protractor with black graduations etched onto the surface in one degree increments. Half circle flat disc 13 is secured to left support arm 12 to keep half circle flat disc 13 in a fixed position. Half circle flat disc 13 has zero degree line on a horizontal plane that run flat across pivot point 4b as shown in figure five. The zero line is on the left and right side of pivot point 4b, a ninety degree line is directly in front of the zero line ninety degrees from zero line at pivot point 4b. Secured to pivot point 4b is dial arm 14. Dial arm 14 is a protractor dial one inch wide and ten inches in length. Dial arm 14 lays flat on the top of half circle flat disc 13 to adjust to the different degree angles of the clavicle on the human body on a horizontal plane. Dial arm 14 can move in a half circle on half circle flat disc 13 to pinpoint degrees etched on half circle flat disc 13. The pivot point for dial arm 14 is pivot point 4b.

The machine of the present invention measures degree angle and anthropometric linear measurements of the skeletal structure of the human body. The individual stands behind the machine with the top of their sternoclavicular joint at 0 degree line. Because every individual is measured from the same beginning point a study can be done according to the data collected. From here 10 componet variables are taken with the measuring unit. These variables are entered into a computer data base for calculation. This now begins an infield study of individual workers at a work station or exercise on a resistance training program and or undergo medical treatment for biomechanical correction. Studying repetitive motion injuries in the work force is one example. (non-surgical). By measuring bone lengths and degree angles of a human body we have found that certain characteristics or trends can be found by this systematic measuring procedure. For example we have found that clients with equal bone lengths in upper legs (femur) and torso length, plus a shorter length in lower leg (tibia) have a 0 degree torso deflection range, these individuals experience chronic low back pain. This means these individuals are at extremely high risk of experiencing a lower lumbar injury that can injure them greatly. 9 other graphs are generated so reaching, bending, twisting, pressing, pulling, and sitting can be broken down into exact biomechanical movements for a specific muscle range group. All measurements are taken with the individual standing behind the measuring unit in a relaxed posture. Every individual is measured from the point of origin or 0 degree line out. This gives the user a systematic way of taking measurements on every individual in the same manner.

The point of origin for all measurements is the top of the sternoclavicular joint, or sternal notch, of the human body. The fixed plexiglass disc 5 has its center point 4a coincident with the point of origin. The radial dial arm 6 pivots about the same center point 4a and therefore measures degree angles from the center point 4a. A slide 3 slides along the radial dial arm 6 and measures lengths from the center point 4a. In this manner any point on the human body is measured with reference to the center point 4a in polar coordinates of degrees and lengths from the center point 4a. The torso rule 2 is also affixed the same point of origin, the center point 4a. The rule slide 1 slides up and down along the torso rule 2 and therefore measures the length of the human torso from the top of the sternum; i.e, the top of the sternoclavicular joint or sternal notch, to the hip socket with reference to the same point of origin. Finally, the depth angle protractor comprising the half circle flat disc 13 and dial arm 14 together measure the degree angle of the clavicle bone on a horizontal plane of the human body.

What is claimed is:

1. In a measuring device used for determining bone lengths and degree angles of the skeletal system of a human body for purposes of determining natural ranges of motion of any specific individual as used in ergonomics, fitness and job safety; a base plate from which a stand extends upwardly, said stand comprising a vertical column attached to said base plate and that has a square tube in said column that extends and adjusts the height of said stand, said square tube having a right support arm that extends right from said square tube, and at the end of said right support arm is a fixed plexiglass disc with black graduations etched on the surface for obtaining degree angles and length measurements of the upper extremities of the human body, further wherein said disc is affixed to said right support arm at a center point which is a point of origin from which all measurements originate and which is the top of the sternoclavicular joint of the human body, and further pivotally affixed to said center point is a plexiglass radial dial arm used in obtaining degree angles of the elbow radius and length measurements of the human body, further attached to said radial dial arm is an aluminum slide that slides along said radial dial arm to indicate the measurements of the human body.

2. In a measuring device as recited in claim 1, further affixed to said center point is an aluminum torso rule in which zero measurement begins at said center point and extends down from said center point for obtaining the measurement of the torso length of the human body.

3. In a measuring device as recited in claim 2, attached to said torso rule is a rule slide that adjusts up and down said torso rule to obtain the measurement of the human torso from top of sternum to hip socket.

4. In a measuring device as recited in claim 1, said tube further having a left support arm that extends left from said tube directly across from said right support arm, and further said left support arm having a depth angle protractor comprising an aluminum half circle flat disc fixed to said left support arm on a horizontal plane with etched black graduations in degree increments for obtaining the degree angle of the clavicle bone on said horizontal plane of the human body.

5. In a measuring device as recited in claim 4, attached to said depth angle protractor is a dial arm which is pivotally attached to a pivot point on said half circle flat disc which is a point of origin of measurements from said depth angle protractor to determine the degree angle of the clavicle bone on said horizontal plane of the human body.

6. In a measuring device used for determining bone lengths and degree angles of the skeletal system of a human body for purposes of determining natural ranges of motion of any specific individual used in ergonomics, fitness and job safety; a base plate from which a stand extends upwardly, said stand comprising a vertical column attached to said base plate and that has a square tube in said column that extends and adjusts the height of said stand, said tube having a right support arm that extends right from said tube, and at the end of said right support arm is a fixed plexiglass disc with black graduations etched on the surface for obtaining degree angles and length measurements of the upper extremities of the human body, and also affixed to said center point is an aluminum torso rule in which zero inches begin at said center point and extends down from said center point for obtaining the measurement of the torso length of the human body.

7. In a measuring device as recited in claim 6, attached to said torso rule, is a rule slide that adjusts up and down said torso rule to obtain the measurement of the human torso from top of sternum to hip socket.

8. In a measuring device as recited in claim 7, said tube further having a left support arm that extends left from said tube directly across from said right support arm, and further said left support arm having a depth angle protractor comprising an aluminum half circle flat disc fixed to said left support arm on a horizontal plane with etched black graduations in one degree increments for obtaining the degree angle of the clavicle bone on a horizontal plane of the human body.

9. In a measuring device as recited in claim 8, attached to said depth angle protractor is a dial arm which is pivotally attached to a pivot point on said half circle flat disc which is a point of origin of measurements from said depth angle protractor to determine the degree angle of the clavicle bone on a horizontal plane of the human body.

* * * * *

UNITED STATES PATENT AND TRADEMARK OFFICE
Certificate

Patent No. 5,586,558                                      Patented: December 24, 1996

On petition requesting issuance of a certificate for correction of inventorship pursuant to 35 U.S.C. 256, it has been found that the above identified patent, through error and without any deceptive intent, improperly sets forth the inventorship. Accordingly, it is hereby certified that the correct inventorship of this patent is:
Daniel R. Riley, Gerald D. Riley, and Gregory Holman.

Signed and Sealed this Twenty-Eighth Day of July, 1998.

JENNIFER BAHR
Supervisory Patent Examiner
Art Unit 3736